United States Patent [19]

Fast

[11] Patent Number: 5,253,652
[45] Date of Patent: Oct. 19, 1993

[54] CYTOLOGIC SAMPLING DEVICE FOR COLLECTING CERVICAL AND VAGINAL CELL SPECIMENS

[76] Inventor: James I. Fast, 7300 N. Monroe St., Hutchinson, Kans. 67502-8921

[21] Appl. No.: 8,492

[22] Filed: Jan. 25, 1993

[51] Int. Cl.⁵ .............................................. A61B 10/00
[52] U.S. Cl. ...................................................... 128/756
[58] Field of Search .......................... 128/749, 756, 759

[56] References Cited

U.S. PATENT DOCUMENTS

| | | | |
|---|---|---|---|
| 2,955,591 | 10/1960 | MacLean | 128/2 |
| 3,626,470 | 12/1971 | Antonides et al. | 128/2 R |
| 3,815,580 | 6/1974 | Oster | 128/2 W |
| 3,877,464 | 4/1975 | Vermes | 128/2 B |
| 3,881,464 | 5/1975 | Levene | 128/2 B |
| 4,127,113 | 11/1978 | Nollan | 128/2 W |
| 4,465,072 | 8/1984 | Takeri | 128/756 |
| 4,700,713 | 10/1987 | Kist | 128/756 |
| 4,754,764 | 7/1988 | Bayne | 128/756 |
| 4,762,133 | 8/1988 | Bayne et al. | 128/756 |
| 4,873,992 | 10/1989 | Bayne | 128/756 |

OTHER PUBLICATIONS

Bergeron and Ferenczy, "Screening Devices for Cervical and Endometrial CA", *Contemporary Ob/Gyn* (1987) pp. 55–66.

*Primary Examiner*—Max Hindenburg
*Attorney, Agent, or Firm*—John R. Flanagan

[57] ABSTRACT

A cytologic sampling device for collecting cervical and vaginal cell specimens from a uterine cervix and vagina. The device includes an elongated flat stem having opposite end portions and a longitudinal portion extending between the opposite end portions. A first brush is disposed on one end portion of the stem for collecting endocervical cell specimens by inserting the one end portion into the vagina and within the mouth of the cervix and rotating the stem with the first brush wiping against the endocervical wall. A third brush is disposed on the other end portion of the stem for collecting vaginal cell specimens by inserting the other end portion into the vagina and wiping the second brush against the vaginal wall. The device also includes an elongated actuator supported on the longitudinal stem portion and having a second brush on one end of the actuator for collecting exocervical cell specimens. By applying finger pressure to a gripping element on an opposite end of the actuator, the actuator is slidably moved relative to the longitudinal stem portion so as to pivot the second brush from a stored position adjacent to the stem, permitting easy entry and removal of the one end portion of the stem into and from the vagina, to a deployed position displaced from the stem, permitting collecting of exocervical cell specimens by the second brush and endocervical cell specimens by the first brush in the same rotational motion of the stem.

20 Claims, 2 Drawing Sheets

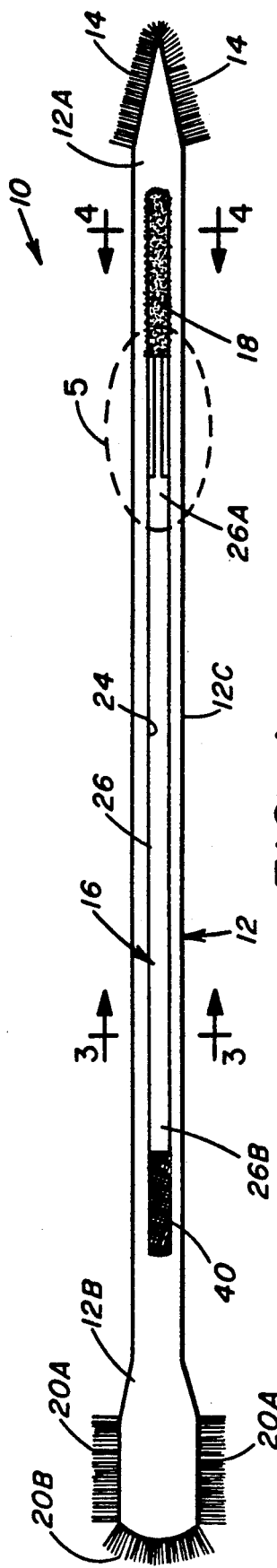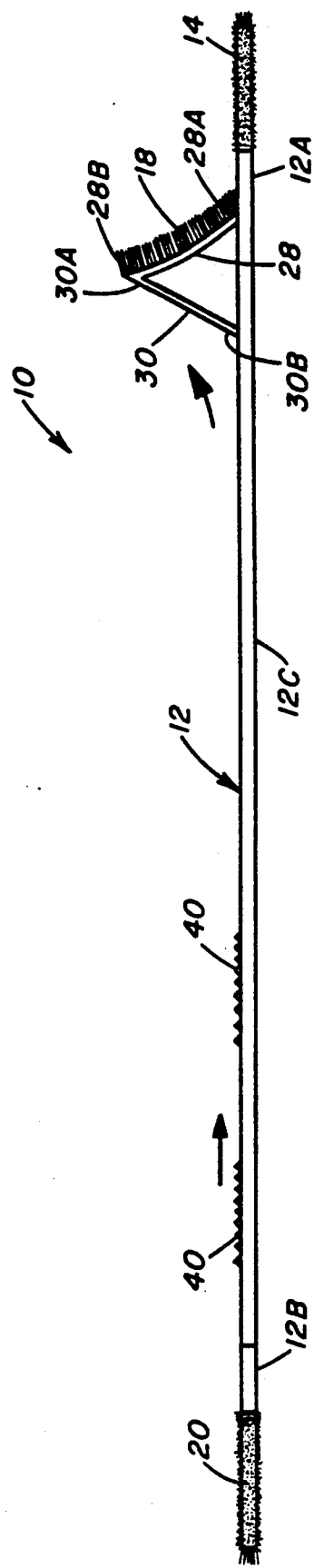

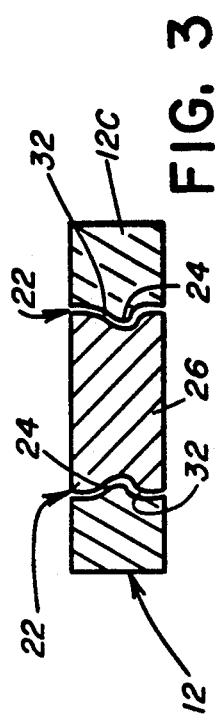
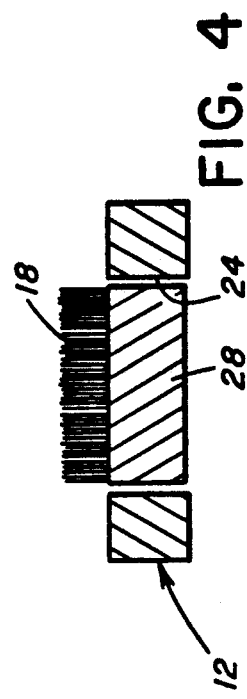
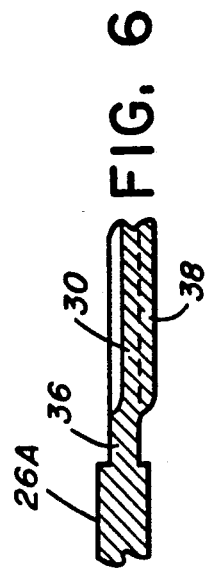
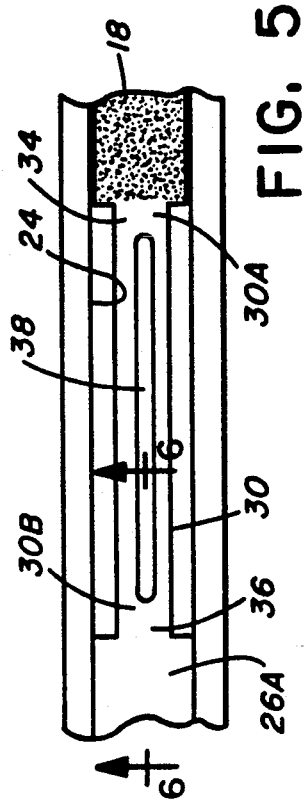
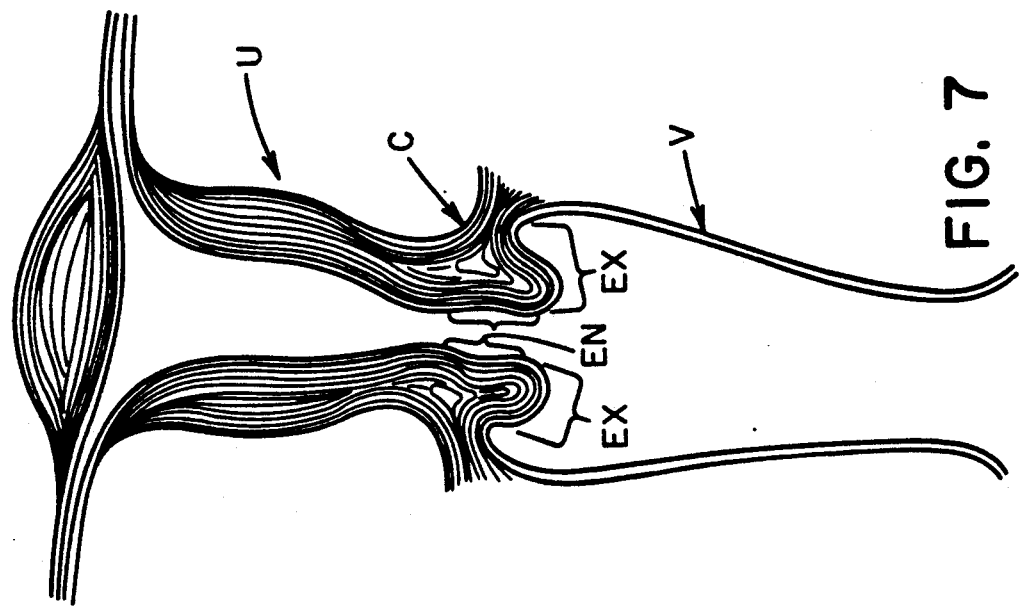

CYTOLOGIC SAMPLING DEVICE FOR COLLECTING CERVICAL AND VAGINAL CELL SPECIMENS

BACKGROUND OF THE INVENTION

1. Field of the Invention

The present invention generally relates to the collecting of cell specimens from a body cavity for diagnostic purposes and, more particularly, is concerned with a cytologic sampling device for collecting both cervical and vaginal cell specimens.

2. Description of the Prior Art

Uterine cervical cancer can be prevented and possibly cured if it is detected early enough, preferably in its precancerous or precursor stages. For this reason, women are encouraged to have examinations on a regular basis. Improvements in early detection devices and techniques will enhance a physician's ability to accurately detect the presence of cancer in its early stages. Accordingly, much effort has been directed to developing such devices.

Bergeron et al in an article entitled "Screening devices for cervical and endometrial Ca", published in *Contemporary OB/GYN* (1987), present an extensive listing of cervical cytologic sampling and screening devices, including wooden spatulas and brushes, and also discuss how the devices should be used to effectively detect the presence of cancer and its precursors. Examples of such devices are also disclosed in U.S. patents to MacLean (U.S. Pat. No. 2,955,591), Antonides (U.S.Pat. No. 3,626,470), Oster (U.S. Pat. No. 3,815,580), Vermes (U.S. Pat. No. 3,877,464), Levene (U.S. Pat. No. 3,881,464), Nollan (U.S. Pat. No. 4,127,113), Kist (U.S. Pat. No. 4,700,713), Bayne (U.S. Pat. No. 4,754,764), Bayne et al (U.S. Pat. No. 4,762,133) and Bayne (U.S. Pat. No. 4,754,764 and 4,873,992).

For a cytologic device to be an effective means to use in sampling and collecting cell specimens for detecting cervical cancer and its precursors, basic criteria must be met. The cytologic device must be simple, easy and quick to use. Also, the device must be accurate, relatively painless, devoid of complications, and relatively inexpensive. While the currently-used devices undoubtedly work as intended, none meet all of the above-mentioned basic criteria.

Also, some devices are susceptible of providing a sample which results in a false negative diagnosis, that is, the specimen which appears to be free of aberrant or malignant cells when in fact such cells are actually present but are not detected. A false negative diagnosis may result when the devices fail to collect the cells or when such cells are collected but not readable, either because they are obscured by the mucus secretions obtained concurrently with the cells or because the cells cannot be adequately stained and accurately read.

Consequently, a need still exists for a cytologic sampling device which more nearly meets the above basic criteria and avoids the susceptibility of providing false negative samples.

SUMMARY OF THE INVENTION

The present invention provides a cytologic sampling device for collecting both cervical and vaginal cell specimens. The device is simple in construction, employs relatively inexpensive materials, is easy and quick to use, and permits making accurate readings and diagnosis by decreasing capillary trauma during sampling. Also, the use of the device is relatively painless to the patient and devoid of complications.

Accordingly, the present invention is directed to a cytologic sampling device for collecting both cervical and vaginal cell specimens from a uterine cervix and vagina. The cytologic sampling device comprises: (a) an elongated stem having a pair of opposite end portions and a longitudinal portion extending between the opposite end portions; (b) first means on one of the pair of end portions of the stem for collecting endocervical cell specimens upon insertion of the one end portion of the stem into a vagina and within the mouth of a cervix; and (c) an actuator mounted on the longitudinal portion of the stem and having second means located adjacent to the first means for collecting exocervical cell specimens, the actuator being movable relative to the longitudinal stem portion for moving the second means between a stored position adjacent to the longitudinal portion to permit entry of said one end portion of the stem into the vagina and a deployed position displaced from the longitudinal portion to permit collecting of the exocervical cell specimens concurrently as the first means collects endocervical cell specimens. The device further comprises (d) third means on the other of the pair of end portions of the stem for collecting vaginal cell specimens upon insertion of the other end portion into the vagina.

The longitudinal portion of the stem includes means defining a track extending between the opposite end portions. The track defining means includes an elongated slot defined in the longitudinal portion of the stem. The slot has a pair of opposite sides with first interengaging means formed therealong. The actuator includes an elongated slide member having a pair of opposite sides with second interengaging means formed therealong being complementary in cross-sectional configuration to the first interengaging means so as to mate therewith and permit longitudinal sliding movement of the slide member along the stem between the opposite end portions thereof.

The actuator also includes a base member pivotally attached at one end to the one end portion of the stem and mounting the second means thereon, and a hinge member having a pair of opposite ends pivotally interconnecting one end of the slide member and a free end of the base member. The hinge member converts longitudinal sliding movement of the slide member relative to the stem into angular pivotal movement of the base member toward and away from the stem.

Also, the hinge member includes a pair of living hinges pivotally connecting the opposite ends of the hinge member respectively to the one end of the slide member and the free end of the base member. Further, the hinge member preferably has a longitudinally-extending stiffening rib formed therein for ensuring that the desired pivotal movement of the base member occurs as a result of the longitudinal sliding movement of the slide member.

The first means is a first plurality of brush elements mounted on the one end portions of the stem in a configuration for collecting endocervical cell specimens upon rotation of the stem and wiping of the first brush elements against the endocervical wall. The second means is a second plurality of brush elements mounted on the base member for collecting exocervical cell specimens upon rotation of the stem and wiping of the second brush elements against the exocervical wall. The third means is a third plurality of brush elements mounted on the other end portion of the stem for collecting vaginal cell specimens upon wiping of the third brush elements against the vaginal wall.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a top plan view of a cytologic sampling device in accordance with the present invention.

FIG. 2 is a side elevational view of the device of FIG. 1.

FIG. 3 is an enlarged cross-sectional view of the device taken along line 3—3 of FIG. 1.

FIG. 4 is another enlarged cross-section view of the device taken along line 4—4 of FIG. 1.

FIG. 5 is an enlarged view of the portion of the device enclosed by the oval 5 of FIG. 1.

FIG. 6 is a longitudinal sectional view taken along line 6—6 of FIG. 5.

FIG. 7 is a schematic sectional view of a uterine cavity.

DETAILED DESCRIPTION OF THE INVENTION

Referring to the drawings, and particularly to FIGS. 1 and 2, there is illustrated a cytologic sampling device of the present invention, generally designated 10. The cytologic sampling device 10 is easily used and manipulated for collecting cervical and vaginal cell specimens from the cervix C and vagina V of the uterus U of a female patient being examined, being depicted schematically in FIG. 7.

Referring to FIGS. 1 and 2, the cytologic sampling device 10 basically includes an elongated stem 12 having opposite end portions 12A, 12B and a longitudinal portion 12C extending therebetween, first means in the form of a first plurality of brush elements 14 mounted on the one end portion 12A of the stem 12 in a generally V-shaped configuration for collecting endocervical cell specimens, and an actuator 16 slidably movably mounted on the longitudinal portion 12C of the stem 12 and having second means in the form of a second plurality of brush elements 18 mounted thereon adjacent to the one end portion 12A of the stem 12 for collecting exocervical cell specimens. The sampling device 10 further includes third means in the form of a third plurality of brush elements 20A mounted on the opposite sides of the end portion 12B of the stem 12 for collecting vaginal cell specimens and brush elements 20B mounted on the end of the end portion 12B for collecting cell specimens from the vagina cuff, if present.

Referring to FIGS. 3–6, the longitudinal portion 12C of the stem 12 includes means defining a track 22 extending between the opposite end portions 12A, 12B of the stem 12. The track 22 includes an elongated slot 24 defined in the longitudinal portion 12C of the stem 12. The slot 24 has a pair of opposite sides with first interengaging means defined therealong in the form a pair of rail-like protrusions 26.

The actuator 16 includes an elongated slide member 26, a base member 28, and a hinge member 30. The slide member 26 is shaped to fit in the slot 24 of the stem 12. The slide member 26 has a pair of opposite sides with second interengaging means defined therealong in the form of a pair of grooves 32 of a complementary cross-sectional shape with respect to the rail-like protrusions 24 on the stem 12 so as to mate therewith and permit longitudinal sliding movement of the slide member 26 along the stem 12 and within the slot 24 between the opposite end portions 12A, 12B of the stem 12.

The base member 28 of the actuator 16 is pivotally attached at one end 28A to the one end portion 12A of the stem 12 and mounts the second brush elements 18 thereon. The hinge member 30 of the actuator 16 has its opposite ends 30A, 30B pivotally interconnecting one end 26A of the slide member 26 and the other free end 28A of the base member 28. The hinge member 30 converts longitudinal sliding movement of the slide member 26 relative to the stem 12 into angular pivotal movement of the base member 28 toward and away from the stem 12.

Preferably, the hinge member 30 includes a pair of living hinges 34, 36 pivotally connecting the opposite ends 30A, 30B of the hinge member 30 respectively to the one end 26A of the slide member 26 and the other free end 28B of the base member 28. Further, the hinge member 30 preferably has a longitudinally-extending stiffening rib 38 formed therein for ensuring that the desired pivotal movement of the base member 28 occurs as a result of the longitudinal sliding movement of the slide member 26.

Referring to FIGS. 1 and 2, the actuator 16 is movable relative to the longitudinal portion 12C of the stem 12 by applying finger pressure to a knurled gripping element 40 defined on the opposite end 26B of the slide member 26 from the hinge member 30. The actuator 16 is slidable for moving the base member 28 and the second brush elements 18 thereon between a stored position (FIG. 1) adjacent to the longitudinal portion 12C to permit entry and removal of the one end portion of the stem 12 into the cavity of the vagina V and into and from the canal of the endocervical region EN of the cervix C (see FIG. 7), and a deployed position (FIG. 2) angularly displaced from the longitudinal portion 12C of the stem 12 to permit collecting of the exocervical cell specimens from the exocervical region EX of the cervix (see FIG. 7) by the second brush elements 18 concurrently as the first brush elements 14 collect endocervical cell specimens.

The configurations of the first and second brush elements 14, 18 facilitate collecting endocervical exocervical cell specimens upon rotation of the stem 12 and wiping of the first and second brush elements 14, 18 against the respective endocervical and exocervical walls after insertion of the one end portion 12A into the cervical canal. The configuration of third brush elements 20 mounted on the other end portion 12B of the stem 12 facilitate collecting vaginal cell specimens upon wiping of the third brush elements 20 against the vaginal wall after insertion of the other end portion 12B into the vaginal cavity. The device 10 permits the accomplishment of vaginal and cervical sampling with the handling of only one instrument by a physician, instead of two instruments as practiced heretofore. Also, the retractability of the second brush elements 18 permits more accurate samples to be obtained and less discomfort for the patient.

The stem 12 and actuator 16 can be made of any suitable semi-flexible disposable plastic material using known fabrication techniques.

It is thought that the present invention and its advantages will be understood from the foregoing description and it will be apparent that various changes may be made thereto without departing from its spirit and scope of the invention or sacrificing all of its material advantages, the form hereinbefore described being merely preferred or exemplary embodiment thereof.

I claim:

1. A cytologic sampling device for collecting cervical cell specimens from a uterine cervix, said device comprising:
   (a) an elongated stem having a pair of opposite end portions and a longitudinal portion extending between said opposite end portions;
   (b) first means on one of said pair of end portions of said stem for collecting endocervical cell specimens upon insertion of said one end portion of said stem into a vagina and within the mouth of a cervix; and
   (c) an actuator mounted on said longitudinal portion of said stem and having second means located adjacent to said first means for collecting exocervical cell specimens, said actuator being movable relative said longitudinal stem portion for moving said second means between a stored position adjacent to said longitudinal portion to permit entry of said one end portion of said stem into the vagina and a deployed position displaced from said longitudinal portion to permit collecting of the exocervical cell specimens concurrently as said first means collects endocervical cell specimens.

2. The device of claim 1 wherein said longitudinal portion of said stem includes means defining a track extending between said opposite end portions.

3. The device of claim 2 wherein said actuator includes an elongated slide member mounted to said track defining means for longitudinal sliding movement along said stem between said opposite ends portions thereof.

4. The device of claim 3 wherein said actuator also includes:
   a base member pivotally attached at one end to said one end portion of said stem and mounting said second means thereon; and
   a hinge member having a pair of opposite ends pivotally interconnecting one end of said slide member and a free end of said base member such that longitudinal sliding movement of said slide member relative to said stem is converted into angular pivotal movement of said base member toward and away from said stem.

5. The device of claim 4 wherein said second means is a second plurality of brush elements mounted on said base member.

6. The device of claim 4 wherein said hinge member includes a pair of living hinges pivotally connecting said opposite ends of said hinge member respectively to said one end of said slide member and said free end of said base member.

7. The device of claim 4 wherein said hinge member has a longitudinally-extending stiffening rib formed therein.

8. The device of claim 2 wherein said track defining means includes an elongated slot defined in said longitudinal portion of said stem, said slot having a pair of opposite sides with first interengaging means formed therealong.

9. The device of claim 8 wherein said actuator includes an elongated slide member having a pair of opposite sides with second interengaging means formed therealong being complementary in cross-sectional configuration to said first interengaging means so as to mate therewith and permit longitudinal sliding movement of said slide member along said stem.

10. The device of claim 1 wherein said first means is a first plurality of brush elements mounted on said one end portions of said stem for collecting endocervical cell specimens.

11. A cytologic sampling device for collecting cervical and vaginal cell specimens from a uterine cervix and vagina, said device comprising:
    (a) an elongated stem having a pair of opposite end portions and a longitudinal portion extending between said opposite end portions;
    (b) first means on one of said pair of end portions of said stem for collecting endocervical cell specimens upon insertion of said one end portion of said stem into a vagina and within the mouth of a cervix;
    (c) an actuator mounted on said longitudinal portion of said stem and having second means located adjacent to said first means for collecting exocervical cell specimens, said actuator being movable relative said longitudinal stem portion for moving said second means between a stored position adjacent to said longitudinal portion to permit entry of said one end portion of said stem into the vagina and a deployed position displaced from said longitudinal portion to permit collecting of the exocervical cell specimens concurrently as said first means collects endocervical cell specimens; and
    (d) third means on the other of said pair of end portions of said stem for collecting vaginal cell specimens upon insertion of said other end portion into the vagina.

12. The device of claim 11 wherein said longitudinal portion of said stem includes means defining a track extending between said opposite end portions.

13. The device of claim 12 wherein said actuator includes:
    an elongated slide member mounted to said track defining means for longitudinal sliding movement along said stem between said opposite ends portions thereof;
    a base member pivotally attached at one end to said one end portion of said stem and mounting said second means thereon; and
    a hinge member having a pair of opposite ends pivotally interconnecting one end of said slide member and a free end of said base member such that longitudinal sliding movement of said slide member relative to said stem is converted into angular pivotal movement of said base member toward and away from said stem.

14. The device of claim 13 wherein said second means is a second plurality of brush elements mounted on said base member.

15. The device of claim 13 wherein said hinge member includes a pair of living hinges pivotally connecting said opposite ends of said hinge member respectively to said one end of said slide member and said free end of said base member.

16. The device of claim 13 wherein said hinge member has a longitudinally-extending stiffening rib formed therein.

17. The device of claim 12 wherein said track defining means includes an elongated slot defined in said longitudinal portion of said stem, said slot having a pair of opposite sides with first interengaging means formed therealong.

18. The device of claim 17 wherein said actuator includes an elongated slide member having a pair of opposite sides with second interengaging means formed therealong being complementary in cross-sectional configuration to said first interengaging means so as to mate therewith and permit longitudinal sliding movement of said slide member along said stem.

19. The device of claim 11 wherein said first means is a first plurality of brush elements mounted on said one end portions of said stem for collecting endocervical cell specimens.

20. The device of claim 11 wherein said third means is a third plurality of brush elements mounted on said other end portion of said stem for collecting vaginal cell specimens.

* * * * *